(12) United States Patent
Honda et al.

(10) Patent No.: US 8,791,427 B2
(45) Date of Patent: Jul. 29, 2014

(54) BIOLOGICAL-SPECIMEN OBSERVATION APPARATUS

(75) Inventors: Susumu Honda, Tokyo (JP); Chika Nakajima, Tokyo (JP)

(73) Assignee: Olympus Corporation, Tokyo (JP)

( * ) Notice: Subject to any disclaimer, the term of this patent is extended or adjusted under 35 U.S.C. 154(b) by 477 days.

(21) Appl. No.: 12/336,124

(22) Filed: Dec. 16, 2008

(65) Prior Publication Data

US 2009/0166570 A1 Jul. 2, 2009

(30) Foreign Application Priority Data

Dec. 26, 2007 (JP) ................................ 2007-333870
Jun. 20, 2008 (JP) ................................ 2008-162127

(51) Int. Cl.
*G21K 5/10* (2006.01)

(52) U.S. Cl.
USPC ...................................................... 250/458.1

(58) Field of Classification Search
USPC ...................................................... 250/458.1
See application file for complete search history.

(56) References Cited

U.S. PATENT DOCUMENTS

| | | | | |
|---|---|---|---|---|
| 4,622,291 | A * | 11/1986 | Picciolo et al. ................... | 435/4 |
| 5,343,018 | A * | 8/1994 | Limbach ....................... | 219/200 |
| 5,650,135 | A | 7/1997 | Contag et al. | |
| 6,832,835 | B2 * | 12/2004 | Matsumoto .................... | 351/206 |
| 7,095,032 | B2 * | 8/2006 | Montagu et al. ............ | 250/458.1 |
| 7,209,287 | B2 * | 4/2007 | Lauer ............................. | 359/368 |
| 7,272,252 | B2 * | 9/2007 | De La Torre-Bueno et al. ............. | 382/133 |
| 7,672,369 | B2 * | 3/2010 | Garakani et al. ......... | 375/240.01 |
| 2003/0082516 | A1 * | 5/2003 | Straus ............................... | 435/4 |
| 2004/0114218 | A1 * | 6/2004 | Karlsson et al. .............. | 359/368 |
| 2005/0211912 | A1 * | 9/2005 | Fox ............................ | 250/458.1 |
| 2008/0051665 | A1 * | 2/2008 | Xu et al. ........................ | 600/476 |
| 2009/0201494 | A1 * | 8/2009 | Furman et al. ............. | 356/237.5 |
| 2010/0207036 | A1 * | 8/2010 | Massonneau et al. ..... | 250/459.1 |

FOREIGN PATENT DOCUMENTS

| | | |
|---|---|---|
| JP | H06-088989 A | 3/1994 |
| JP | 2003-536052 | 12/2003 |
| JP | 2005-316362 | 11/2005 |
| JP | 2006-039048 A | 2/2006 |

(Continued)

OTHER PUBLICATIONS

Japanese Office Action dated Jul. 3, 2012 issued in corresponding Japanese Patent Application No. 2008-162127.

*Primary Examiner* — Christine Sung
(74) *Attorney, Agent, or Firm* — Scully, Scott, Murphy & Presser, P.C.

(57) ABSTRACT

The distribution of a fluorescent material in a specimen can be observed and the fluorescent material can be obtained as clear, highly quantitative image data. A biological-specimen observation apparatus is provided which comprises a stage on which a specimen is mounted; a position detector, provided on the stage, that detects the position of the specimen; a light source that emits excitation light or illumination light onto the specimen mounted on the stage; an objective lens, disposed opposing the stage, that collects fluorescence or reflected light from the specimen; an image-forming lens that forms an image on the specimen, collected by the objective lens; an image acquisition unit that acquires the image on the specimen, formed by the image-forming lens; an image storage unit that stores the image obtained by the image acquisition unit and positional information of the specimen detected by the position detector in association with each other; and an image processing unit that performs combining processing of a plurality of the images stored by the image storage unit on the basis of the positional information stored in association with the images.

16 Claims, 20 Drawing Sheets

(56) References Cited

FOREIGN PATENT DOCUMENTS

| JP | 2006-154230 A | 6/2006 |
|---|---|---|
| JP | 2006-518050 A | 8/2006 |
| JP | 2006-284965 A | 10/2006 |
| WO | WO 01/63247 | 8/2001 |
| WO | 2004/075107 A2 | 7/2012 |

* cited by examiner

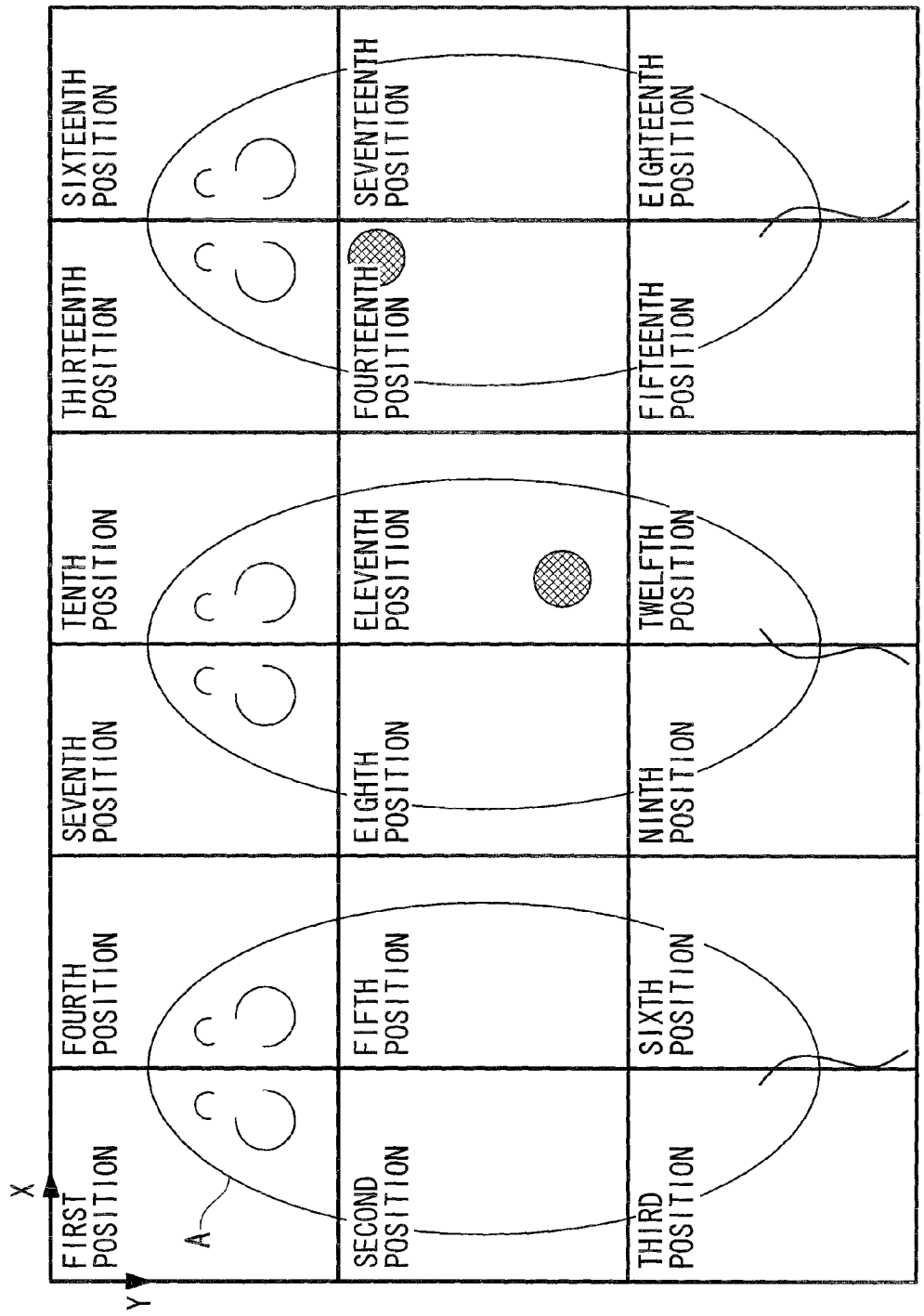

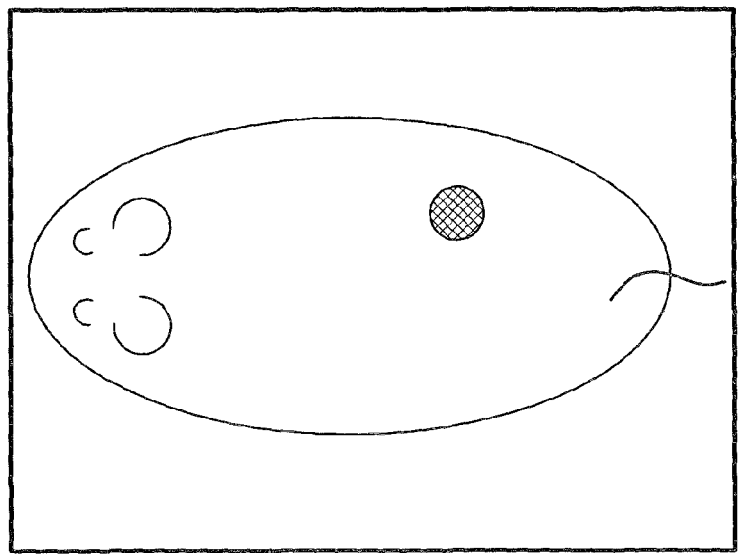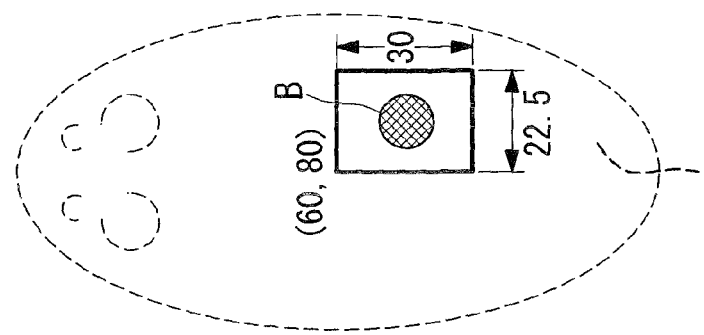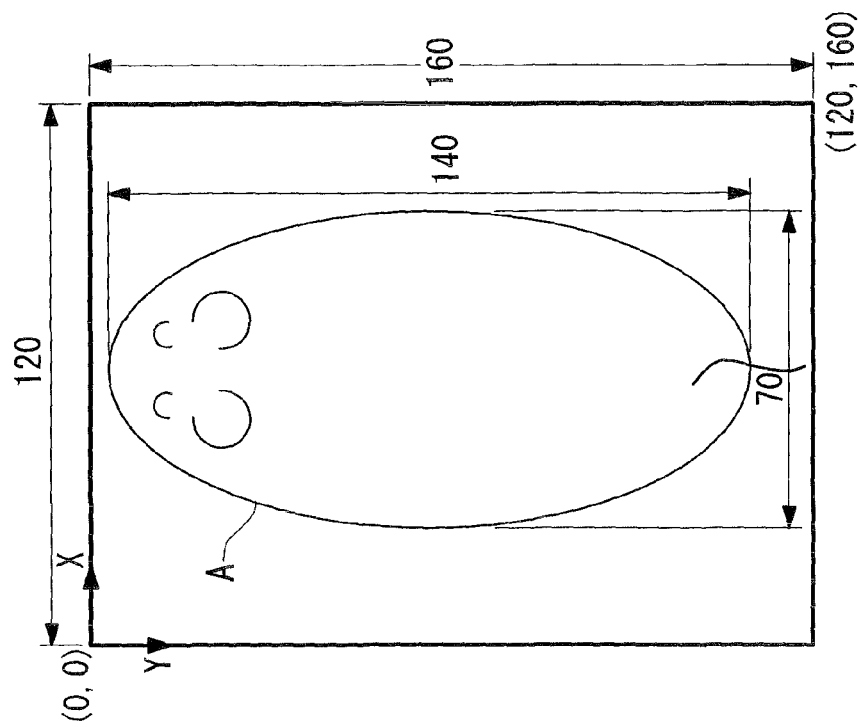

US 8,791,427 B2

BIOLOGICAL-SPECIMEN OBSERVATION APPARATUS

BACKGROUND OF THE INVENTION

1. Field of the Invention

The present invention relates to a biological-specimen observation apparatus.

This application is based on Japanese Patent Application Nos. 2007-333870 and 2008-162127, the content of which is incorporated herein by reference.

2. Description of Related Art

A known observation apparatus in the related art is capable of both observation of the distribution of a fluorescent material in a specimen and acquisition of clear, highly quantitative images of the fluorescent material by switching between an objective lens and an image-forming lens to achieve a broad range of magnification (for example, refer to Japanese Unexamined Patent Application, Publication No. 2005-316362).

Furthermore, a known image acquisition apparatus in the related art displays the distribution of a fluorescent material in a specimen by obtaining and storing a bright field image and a luminous image and automatically generating an image in which the two images are superimposed (for example, refer to Japanese Translation of PCT International Application, Publication No. 2003-536052).

Another known observation apparatus performs time-series contrast observation of a fluorescence image that contains an entire specimen (for example, refer to U.S. Pat. No. 5,650,135).

However, the observation apparatus disclosed in Japanese Unexamined Patent Application, Publication No. 2005-316362 has a disadvantage of being unable to associate an image showing the distribution of a fluorescent material and a clear, highly quantitative image of the fluorescent material with each other.

The image acquisition apparatuses disclosed in Japanese Translation of PCT International Application, Publication No. 2003-536052 and the observation apparatuses disclosed in U.S. Pat. No. 5,650,135 have a disadvantage of being unable to perform clear, highly quantitative fluorescence observation because they observe a specimen using a macro-image in which an entire specimen is acquired.

BRIEF SUMMARY OF THE INVENTION

The present invention is made in consideration of the above-described circumstances. Accordingly, it is an object of the present invention to provide a biological-specimen observation apparatus that allows observation of the distribution of a fluorescent material in a specimen and acquisition of the fluorescent material as clear, highly quantitative image data.

To achieve the above object, the present invention provides the following solutions.

According to an aspect of the present invention, a biological-specimen observation apparatus is provided which comprises a stage on which a specimen is mounted; a position detector, provided on the stage, that detects the position of the specimen; a light source that emits excitation light or illumination light onto the specimen mounted on the stage; an objective lens, disposed opposing the stage, that collects fluorescence or reflected light from the specimen; an image-forming lens that forms an image on the specimen, collected by the objective lens; an image acquisition unit that acquires the image on the specimen, formed by the image-forming lens; an image storage unit that stores the image obtained by the image acquisition unit and positional information of the specimen detected by the position detector in association with each other; and an image processing unit that performs combining processing of a plurality of the images stored by the image storage unit on the basis of the positional information stored in association with the images.

In the above aspect, a diaphragm device capable of changing an aperture diameter may be provided between the objective lens and the image-forming lens.

In the above aspect, there may be provided a focus detecting unit that detects focusing of the objective lens on the specimen; and an autofocusing unit that moves the stage in a direction along an optical axis of the objective lens on the basis of the detection result of the focus detecting unit so as to focus the objective lens on the specimen.

In the above aspect, a zooming mechanism for changing zoom magnification may be provided between the objective lens and the image-forming lens; wherein the image storage unit may store the zoom magnification in association with the images and the positional information.

In the above aspect, the image acquisition device may be a CCD camera, the observation apparatus having a function for changing an image acquisition region of the CCD camera and further comprising an information recording unit that records the obtained image acquisition region.

In the above aspect, the image processing unit may have a function for trimming part of the stored images and combining processing them.

In the above aspect, the image processing unit may have a deconvolution function.

In the above aspect, the image processing may include at least the process of superimposing a bright field image and a fluorescence image.

In the above aspect, the fluorescence image combined by the image processing unit may be subjected to image processing for changing the color in accordance with the brightness value.

The present invention offers the advantages in that the distribution of a fluorescent material in a specimen can be observed and the fluorescent material can be obtained as clear, highly quantitative image data.

BRIEF DESCRIPTION OF THE SEVERAL VIEWS OF THE DRAWINGS

FIG. 6 is a diagram showing an example image obtained by the biological-specimen observation apparatus having the stage in FIG. 5;

FIG. 9A is a diagram showing an example image obtained by the biological-specimen observation apparatus in FIG. 8, showing a combined image of the whole image of a specimen and the image of a fluorescent material;

FIG. 9B is a diagram showing an example image obtained by the biological-specimen observation apparatus in FIG. 8, showing a combined image of the image of a fluorescent material of a specimen and the image of a fluorescent material;

FIG. 9C is a diagram showing an example image obtained by the biological-specimen observation apparatus in FIG. 8, showing a combined image of the whole image and the image of a fluorescent material;

DETAILED DESCRIPTION OF THE INVENTION

Referring to FIGS. 1 to 4C, a biological-specimen observation apparatus 1 according to a first embodiment of the present invention will be described hereinbelow.

Figure 1:
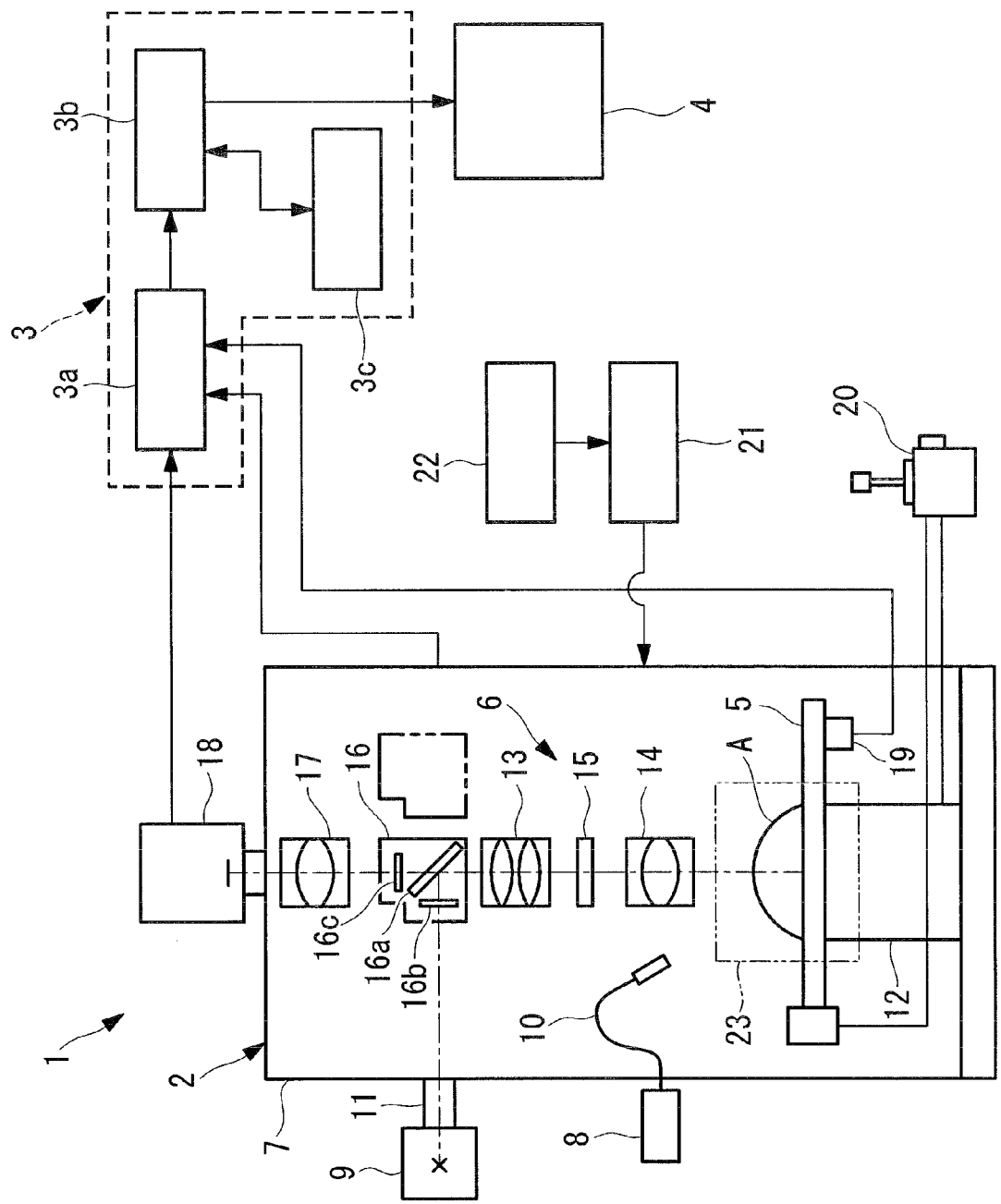
FIG. 1 is a diagram showing the overall configuration of a biological-specimen observation apparatus according to a first embodiment of the present invention.

As shown in FIG. 1, the biological-specimen observation apparatus 1 according to this embodiment is provided with an observation-apparatus main body 2, a control unit 21 that controls the observation apparatus, an operation storage unit 22 that provides a predetermined operation program to the control unit 21, an image control unit 3, and a display 4. The observation-apparatus main body 2 is provided with a stage 5 on which a specimen A, such as a small laboratory animal, for example, a mouse, is mounted, an observation optical system 6, and a case 7 that accommodates the observation optical system 6 to shield it from light.

The observation optical system 6 is provided with a visible-light source 8 that emits visible light for bright-field observation, an excitation-light source 9 that emits excitation light for fluorescence observation, a light transfer member 10 that guides the visible light from the visible-light source 8 to the specimen A, a phototransmitting tube 11 that guides the excitation light from the excitation-light source 9 to the specimen A, a focusing mechanism 12 that adjusts the focal point of the specimen A, a zooming optical system 13 that adjusts the observation magnification, an objective lens 14 that emits the visible light and the excitation light onto the specimen A on the stage 5 and collects reflected light of the visible light returning from the specimen A and fluorescence, a diaphragm 15 that can change the beam diameter of the light collected by the objective lens 14, a dichroic unit 16 that separates the reflected light and the fluorescence collected by the objective lens 14 from the excitation light, an image-forming lens 17 that focuses the reflected light and the fluorescence collected by the objective lens 14 and separated by the dichroic unit 16 to form an image, and an image acquisition unit 18 that acquires an image of the specimen A formed by the image-forming lens 17.

The stage 5 is an electrically driven stage, and the focusing mechanism 12 is an electrically driven focusing mechanism. The stage 5 and the focusing mechanism 12 can operate in response to signals from the control unit 21 and can also move to a desired position in response to signals from an external operating unit 20.

The operating unit 20 is provided with a joystick for operating the stage 5 and a knob for operating the focusing mechanism 12.

Figure 2:
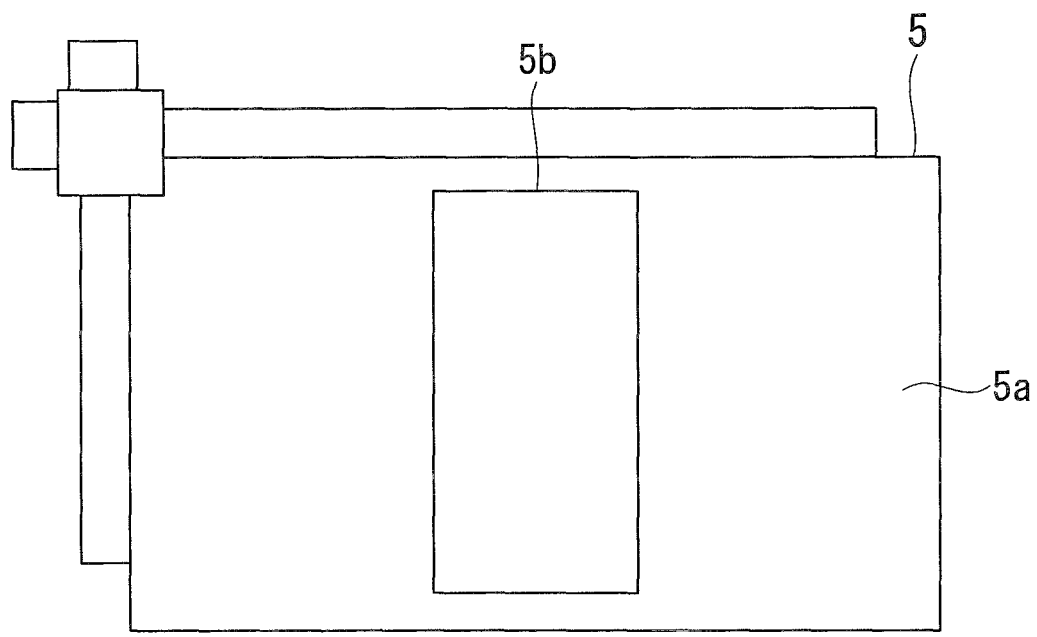
FIG. 2 is a plan view showing a stage of the biological-specimen observation apparatus in FIG. 1.

Furthermore, the stage 5 is provided with a position detector 19. Positional information detected by the position detector 19 is sent to an information recording section 3a. As shown in FIG. 2, an observation region is indicated on the upper surface 5a by an indicating line 5b in a color different from an upper surface 5a of the stage 5. Heat insulating unit is provided inside the indicating line 5b so as to keep the specimen A around 37° C. A holding mechanism for holding a mouthpiece for feeding anesthetic or oxygen to the specimen A is provided slightly inside the short side of the indicating line 5b.

The case 7 has an opening 23 closed and opened by a door, for taking the specimen A in and out, in the vicinity of the specimen A.

The dichroic unit 16 is provided with a dichroic mirror 16a that reflects excitation light and allows fluorescence and reflected light to pass through and band-pass filters 16b and 16c disposed on the excitation-light source 9 side and the image-forming lens 17 side, with the dichroic mirror 16a therebetween, to allow light of a specified wavelength to selectively pass through. The characteristics of the dichroic mirror 16a and the band-pass filters 16b and 16c are adjusted to match the wavelength characteristics of the fluorescent material to be observed.

The dichroic unit 16 is disposed in such a manner that it can be inserted in and removed from an optical axis by means of a rotary turret mechanism, for example. A plurality of dichroic units 16 with different characteristics may be provided and may be freely inserted in or removed from the observation optical system 6. Furthermore, the excitation-light source 9 can be used as a visible-light source by setting the characteristics of the band-pass filters 16b and 16c on the excitation-light source 9 side to the entire visible band (for example, from 400 to 600 nm) and by using the dichroic mirror 16a as a half mirror.

The control unit 21 is configured to control the focusing mechanism 12, the stage 5, the diaphragm 15, the zooming optical system 13, the insertion and removal of the dichroic unit 16, the image acquisition unit 18, the visible-light source 8, and the excitation-light source 9 of the observation-apparatus main body 2. All of them can be electrically controlled and can be operated in accordance with electrical signals from the control unit 21.

The image control unit 3 is provided with the information recording section 3a that associates an image obtained by the image acquisition unit 18 with information from the observation-apparatus main body 2 and information from the position detector 19 of the stage 5, an image storage section 3b that stores the image associated with the information, and an image processing section 3c that processes the image.

The operation of the biological-specimen observation apparatus 1 with this configuration according to this embodiment will be described with reference to FIGS. 3A and 3B.

The specimen A is set on the stage 5 through the opening 23; the opening 23 is closed by closing the door; and the focusing mechanism 12 is operated to focus the specimen A irradiated by the visible-light source 8 while a live image obtained by the image acquisition unit 18 is being observed. In obtaining the live image, the obtained image passes through the information recording section 3a and the image storage section 3b and is displayed on the display 4 in real time.

At that time, the diaphragm 15 limits the beam to a small diameter. After focusing, a program stored in the operation storage unit 22 is started so that a plurality of continuous adjacent bright field images is obtained. The images obtained by the image acquisition unit 18 are sent to the information recording section 3a and are stored in the image storage section 3b in association with the positional information of the stage 5 and the information of the observation-apparatus main body 2.

After completing acquisition and recording of the plurality of images, the plurality of images are sent to the image processing section 3c and combined into one image on the basis of the positional information of the stage 5, stored in association with the images. The combined image is stored in the image storage unit 3b and is displayed on the display unit 4.

Next, the visible-light source 8 is turned off, and the excitation-light source 9 is turned on to observe a fluorescence image. At that time, a desired dichroic unit 16 is used according to the characteristics of fluorescence to be observed. The diaphragm 15 is opened to the maximum. As in observation of bright field images, the fluorescence image is focused on while being observed by the image acquisition unit 18.

After focusing, the operating unit 20 is operated to move the stage 5 so that the fluorescent material to be observed comes to the center of the field of view. Thereafter, the zooming optical system 13 is operated to set a desired magnification in accordance with the size of the fluorescent material. After the specimen A has been moved and the magnification has been set, focusing is performed again.

After completing positioning, magnification setting, and focusing, a fluorescence image is obtained by the image acquisition unit 18. The image obtained by the image acquisition unit 18 is sent to the information recording section 3a and is stored in the image storage section 3b in association with the positional information of the stage 5 and the information of the observation-apparatus main body 2, and is then displayed on the display 4.

Furthermore, the combining process of retrieving the plurality of images stored in the image storage section 3b and superposing them is performed by the image processing section 3c. When superposing the images in the image processing section 3c, the images are combined using positional information and magnification information stored in association with the images. The combined image is stored in the image storage section 3b and displayed on the display 4.

A series of these operations is introduced by a wizard function in response to input of a start signal to the control unit 21 and is executed semiautomatically. The fluorescence image may be displayed in a rainbow, with the color changed according to the brightness value.

Figure 3A:
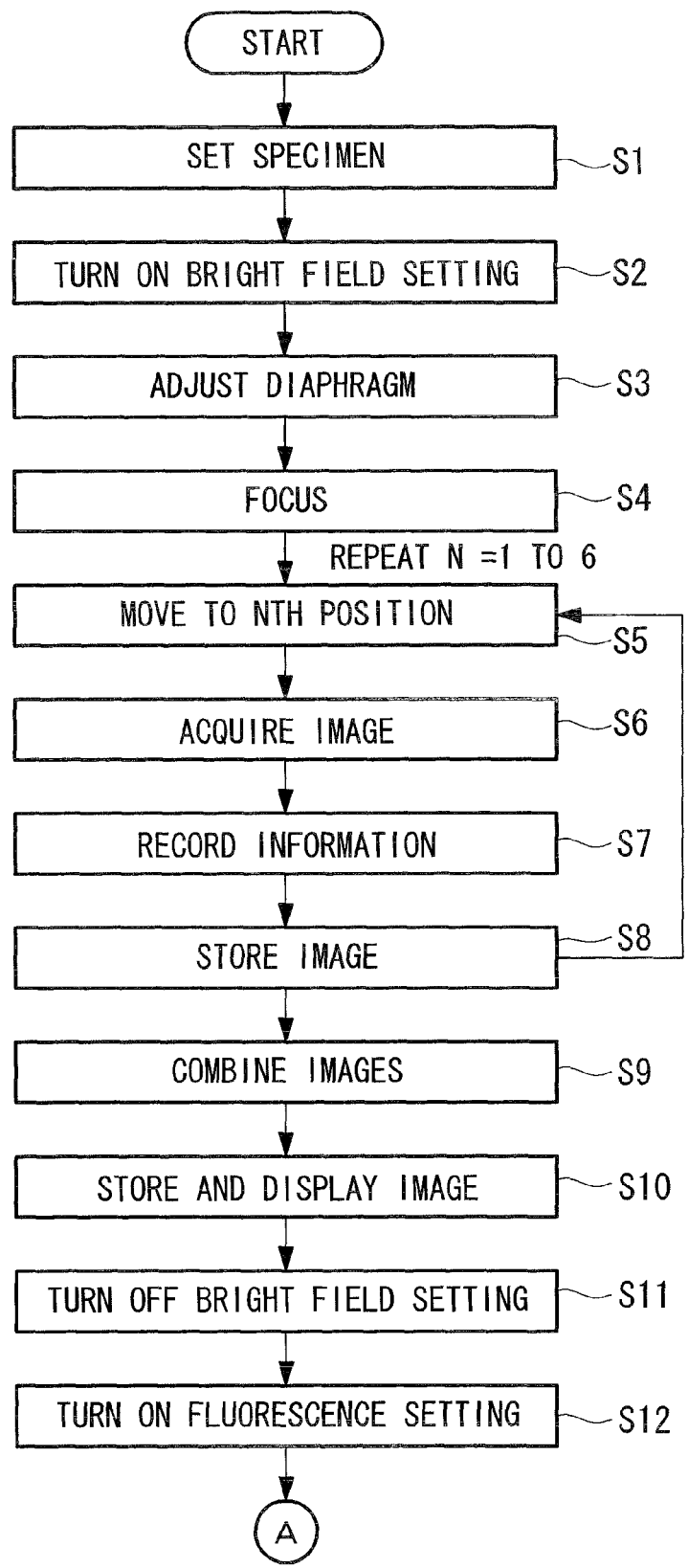
FIG. 3A is a flowchart describing the operation of the biological-specimen observation apparatus in FIG. 1.
Figure 3B:
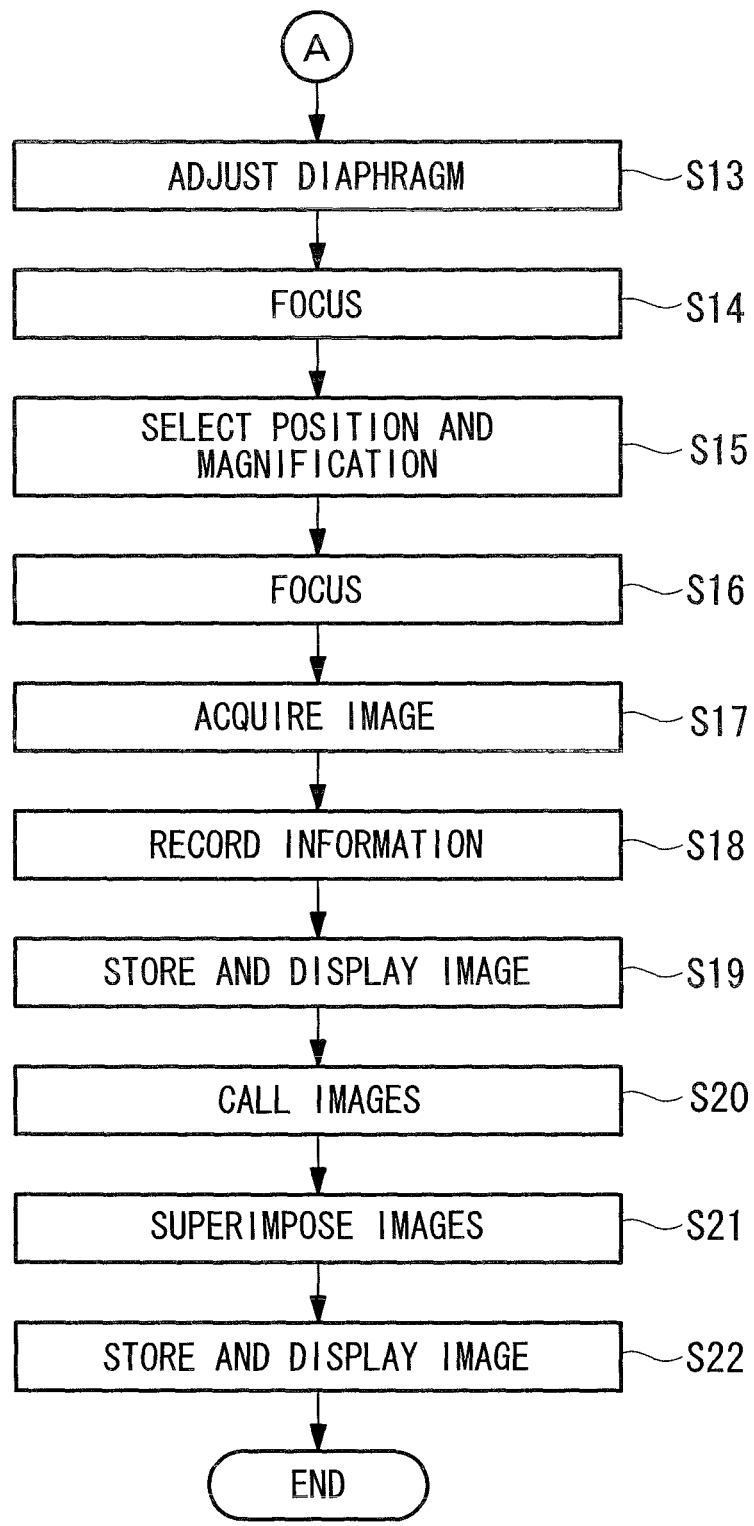
FIG. 3B is a flowchart describing the operation of the biological-specimen observation apparatus in FIG. 1.
Figure 4C:
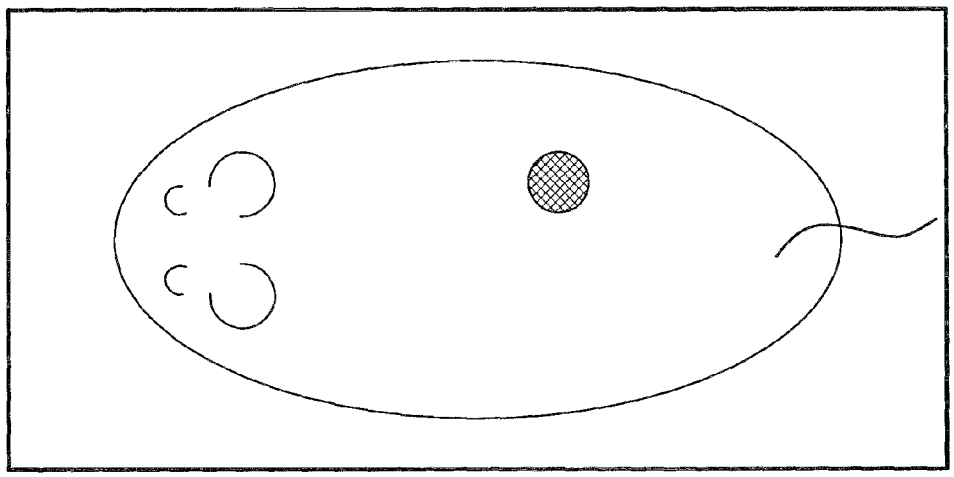
FIG. 4C is a diagram showing an example image obtained by the operation according to the flowchart in FIGS. 3A and 3B, showing a combined image of the whole image and the image of a fluorescent material.
Figure 4B:
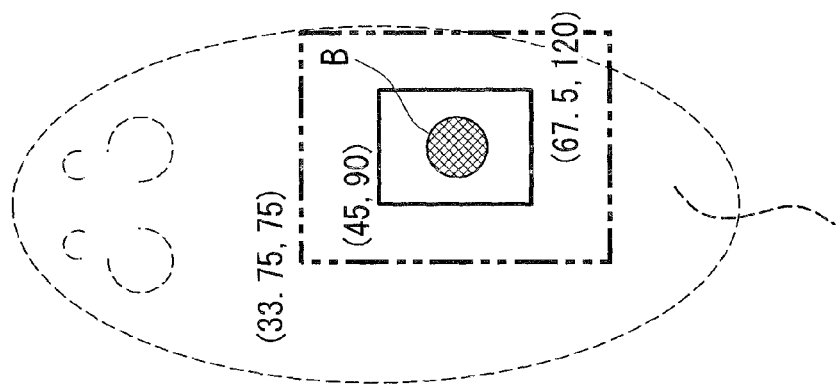
FIG. 4B is a diagram showing an example image obtained by the operation according to the flowchart in FIGS. 3A and 3B, showing a combined image of the image of a fluorescent material of a specimen and the image of a fluorescent material.
Figure 4A:
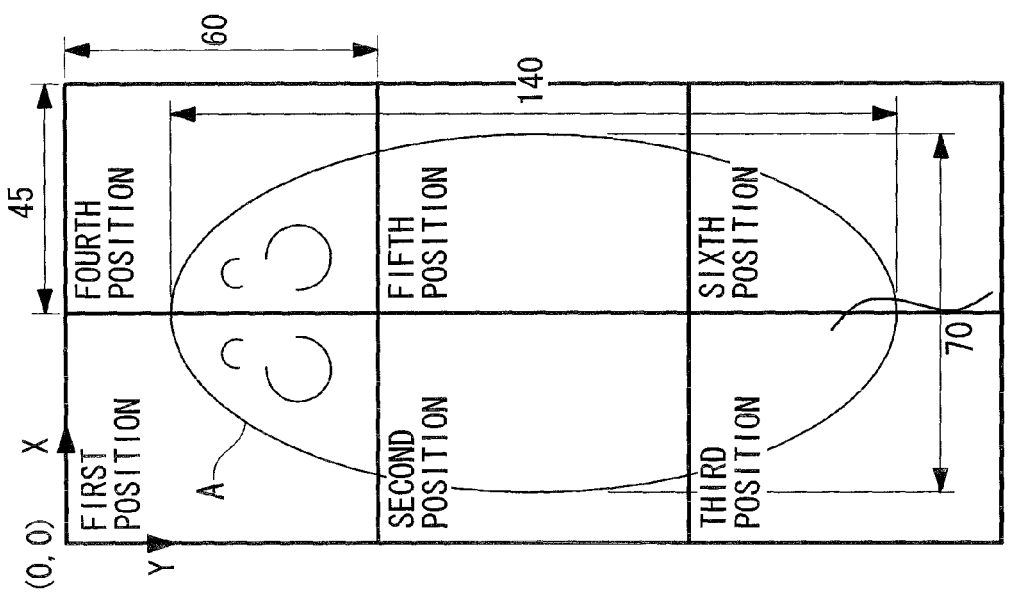
FIG. 4A is a diagram showing an example image obtained by the operation according to the flowchart in FIGS. 3A and 3B, showing a combined image of the whole image of a specimen and the image of a fluorescent material.

Referring to FIGS. 4A, 4B and 4C, the flowchart in FIGS. 3A and 3B will be described in more detail.

FIG. 4A is used to describe steps S1 to S11 of the flowchart in FIG. 3A.

First, assuming that the size of the specimen A is 40×140 mm, the observation viewing region is 45×60 mm, and assuming that the image acquisition unit 18 is a ⅔-inch CCD camera, the projection magnification is about ×0.14.

In step S1, an observer sets the specimen A using the indicating line 5b provided on the stage 5. "Turn on bright field setting" in step S2 indicates a state in which the visible-light source 8 is turned on and the dichroic unit 16 is removed from the observation optical system 6. "Turn off bright field setting" in step S11 is opposite thereto.

In step S3, the diaphragm 15 is adjusted to reduce the beam diameter of an afocal optical system behind the objective lens 14 to about 10 mm (50%). In step S4, the observer performs focusing the operating unit 20.

First, at N=1, the stage 5 is moved to the first position (step S5).

Then, the position detector 19 of the stage 5 recognizes coordinates (0, 0). Image-acquisition is performed in this state (step S6), and the acquired image is associated with the coordinates (0, 0) of the upper left end. Furthermore, coordinates (0, 60) of the lower left end of the image, coordinates (45, 0) of the upper right end, and coordinates (45, 60) of the lower right end are associated by ascertaining the magnification information of the observation-apparatus main body 2 (step S7) In this way, the image with associated coordinates is stored in the image storage section 3b (step s8).

Next, N is incremented to N=2, and the stage 5 is moved by a programmed moving amount X=0 mm and Y=60 mm to the second position (step S5).

Then, the position detector 19 of the stage 5 recognizes coordinates (0, 60). Image-acquisition is performed in this state (step S6), and the acquired image is associated with the coordinates (0, 60) of the upper left end. Furthermore, coordinates (0, 120) of the lower left end of the image, coordinates (45, 60) of the upper right end, and coordinates (45, 120) of the lower right end are associated by ascertaining the magnification information of the observation-apparatus main body 2 (step S7). In this way, the image with associated coordinates is stored in the image storage section 3b (step S8).

After this operation is repeated until N reaches N=6, six images from the first position to the sixth position shown in FIG. 4A are stored in the image storage section 3b.

The six images from the first position to the sixth position are read from the image storage section 3b and are combined by the image processing section 3c in such a manner that the coordinates of the individual corners agree, to generate one combined image (step S9). The coordinates of the four corners of the combined image, that is, the coordinates (0, 0) of the upper left end, the coordinates (90, 0) of the upper right end, the coordinates (0, 180) of the lower left end, and the coordinates (90, 180) of the lower right end, are stored in the image storage section 3c in association with the image, and the image is displayed on the display 4 (step S10).

Next, "turn off bright field setting" is executed (step S11), and the excitation-light source 9 is turned on to allow selection of the dichroic unit 16 (step S12). The observer sends a signal from the control unit 21 to select a desired dichroic unit 16 and dispose it in the observation optical system 6.

Next, the diaphragm 15 is opened to an aperture diameter of about 20 mm (100%) in aperture diameter (step S13), and focusing is performed (step S14).

The planar position of the specimen A is adjusted by the operator using the operating unit 20, and the zooming optical system 13 is operated in accordance with a signal from the control unit 21 so as to acquire a fluorescent material B at a desired position and in a desired size (step S15).

Then, after focusing has been performed again (step S16), an image is obtained (step S17) and stored in association with the positional information of the four corners of the image on the basis of the positional information from the position detector 19 and the magnification information from the observation-apparatus main body 2 (steps S18 and S19). For example, as shown in FIG. 4B, in the case where the stage 5 is moved so that the upper left end of the observation region is set to (33.75, 75), and zooming is set at ×2, the upper left end of the image is stored as (45, 90). Here, the fluorescence-image acquisition processing from step S16 to S20 is performed by the observer a desired number of times (two or more times).

Thereafter, the images stored in steps S10 and S19 are retrieved (step S20), and the fluorescence image stored in step S19 is superimposed on the bright field image combined in step S10 (step S21). At that time, the images are superimposed such that the coordinates stored in association with the image in step S10 and the coordinates stored in association with the image in step S19 are aligned. The image superimposed as shown in FIG. 4C is stored in the image storage section 3b and displayed on the display 4 (step S22).

Thus, the biological-specimen observation apparatus 1 according to this embodiment can acquire an accurate bright field image and an image in which a clear fluorescence image is superimposed at an accurate position of the bright field image. This offers the advantage of allowing a fluorescent material in the specimen A to be clearly observed and the distribution of the fluorescent material in the specimen A to be quantitatively observed.

Figure 5:
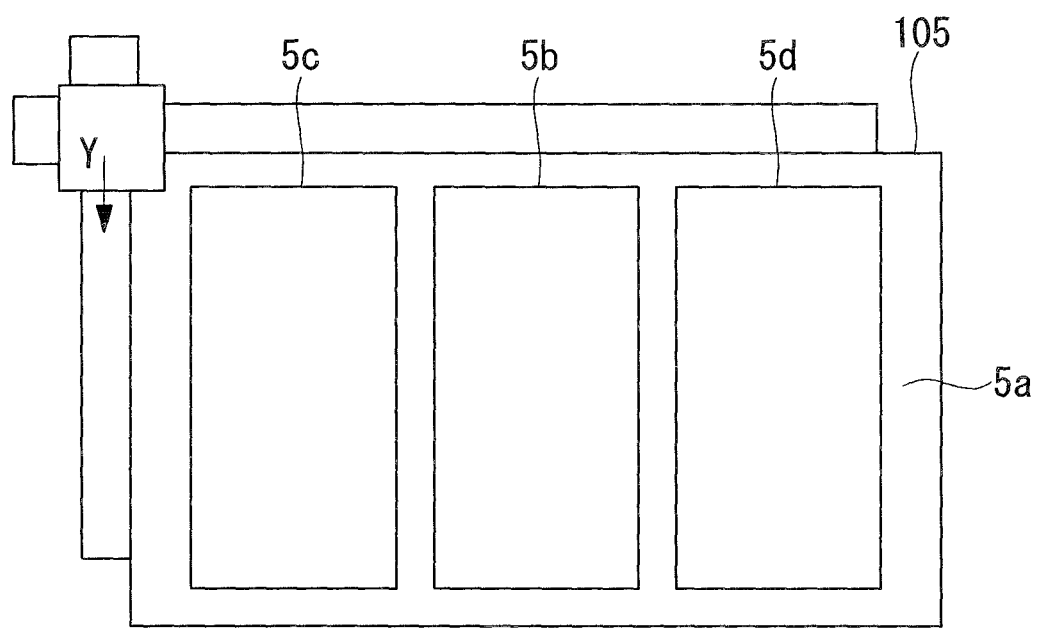
FIG. 5 is a plan view of a modification of the stage of the biological-specimen observation apparatus in FIG. 1.

Although this embodiment shows the stage 5 having the indicating line 5b for mounting one specimen A by way of example, a stage 105 having a plurality of indicating lines 5b to 5d for mounting two or more specimens A may be adopted, as shown in FIG. 5. The indicating lines 5b to 5d are arranged in the X direction at intervals of about 15 mm.

In setting the specimens A, three specimens A are set in accordance with the indicating lines 5b to 5d. The program in the operation storage unit 22 is configured so that positions 1 to 18 are obtained as shown in FIG. 6. The other operations are the same as those of the flowchart in FIGS. 3A, 3B and 3C.

This allows acquisition of an image in which a image of the fluorescence material that the observer desires is superimposed on a bright field image in which three specimens A are arranged side-by-side.

This configuration offers the same advantages as the above-described embodiment and also the advantage of improving the throughput and allowing comparison among the specimens A by obtaining three specimens A at the same time.

Although this embodiment adopts the dichroic unit 16 having the dichroic mirror 16a and the band-pass filters 16b and 16c, a combination with a tunable filter 401 may be adopted.

Figure 7A:
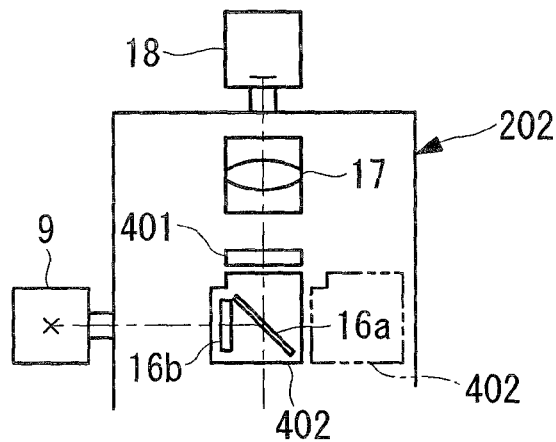
FIG. 7A is a diagram showing a modification of a dichroic unit of the biological-specimen observation apparatus in FIG.

As shown in FIG. 7A, the tunable filter 401 is disposed between a dichroic unit 402 that supports the dichroic mirror 16a and the band-pass filter 16b and the image-forming lens 17. The tunable filter 401 selects the transmission wavelength of fluorescence that is emitted from the specimen A and passes through the dichroic mirror 16a.

The tunable filter 401 is a filter that can change the transmission wavelength in accordance with an electrical signal. The transmission wavelength changes in accordance with a signal from the control unit 21. In this case, the image processing section 3c needs an unmixing function for analyzing a partial wavelength characteristic of an obtained image to discriminate a fluorescent element.

At the image-acquisition step S17 in FIG. 3, a plurality of images whose fluorescence wavelengths are shifted by the tunable filter 401 is obtained. Furthermore, in the superimposing step S21, the plurality of the fluorescence images is superimposed and subjected to unmixing so that a fluorescent element is discriminated. This allows acquisition of a clear image and discrimination of a fluorescent element.

Figure 7B:
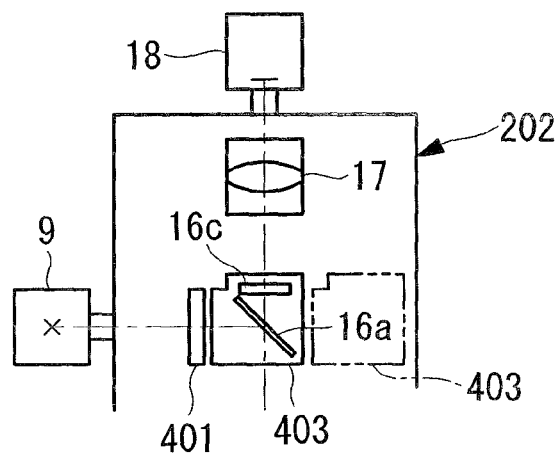
FIG. 7B is a diagram showing a modification of the dichroic unit of the biological-specimen observation apparatus in FIG. 1.

As shown in FIG. 7B, the tunable filter 401 may be disposed between the excitation-light source 9 and a dichroic unit 403. In this case, the dichroic unit 403 has the dichroic mirror 16a and the band-pass filter 16c. Changing the excitation wavelength using the tunable filter 401 allows wavelength analysis. With this configuration, the fluorescence transmission wavelength does not change, thus offering the advantage of causing no focus shift due to chromatic aberration of a fluorescence image.

Figure 7C:
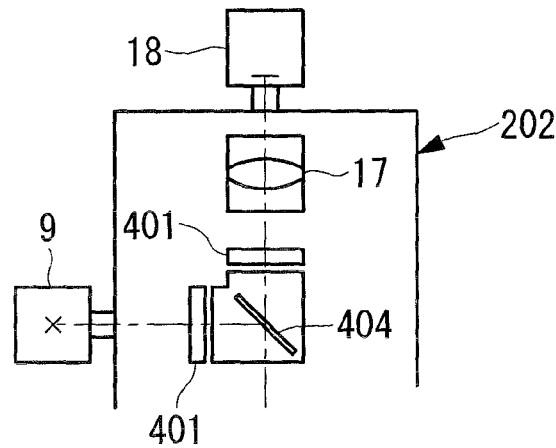
FIG. 7C is a diagram showing a modification of the dichroic unit of the biological-specimen observation apparatus in FIG. 1.
Figure 7D:
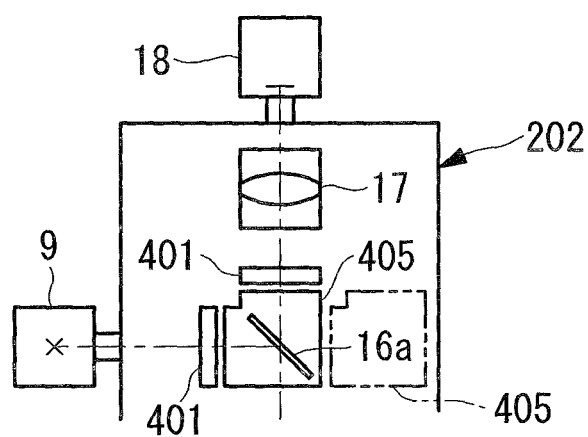
FIG. 7D is a diagram showing a modification of the dichroic unit of the biological-specimen observation apparatus in FIG. 1.

As shown in FIG. 7C, a half mirror 404 and tunable filters 401 disposed between the half mirror 404 and the excitation-light source 9 and between the half mirror 404 and the image-forming lens 17 may be disposed in place of the dichroic units 402 and 403. In this case, there is no need to provide a large number of dichroic mirrors 16a, offering the advantage of eliminating the need for insertion and removal thereof. As shown in FIG. 7D, in the case where a dichroic unit 405 having the dichroic mirror 16a in place of the half mirror 404 is disposed, the dichroic unit 405 may be detachably attached in accordance with the excitation wavelength and the fluorescence wavelength. This allows the excitation wavelength and the fluorescence wavelength to be selected freely, permitting acquisition of a fluorescence image suitable for a desired fluorescent dye.

Referring to FIGS. 8, 9A, 9B and 9C, a biological-specimen observation apparatus 201 according to a second embodiment of the present invention will be described hereinbelow.

In the description of this embodiment, components having a configuration common to the above-described biological-specimen observation apparatus 1 according to the first embodiment are given the same reference numerals, and descriptions thereof will be omitted.

Figure 8:
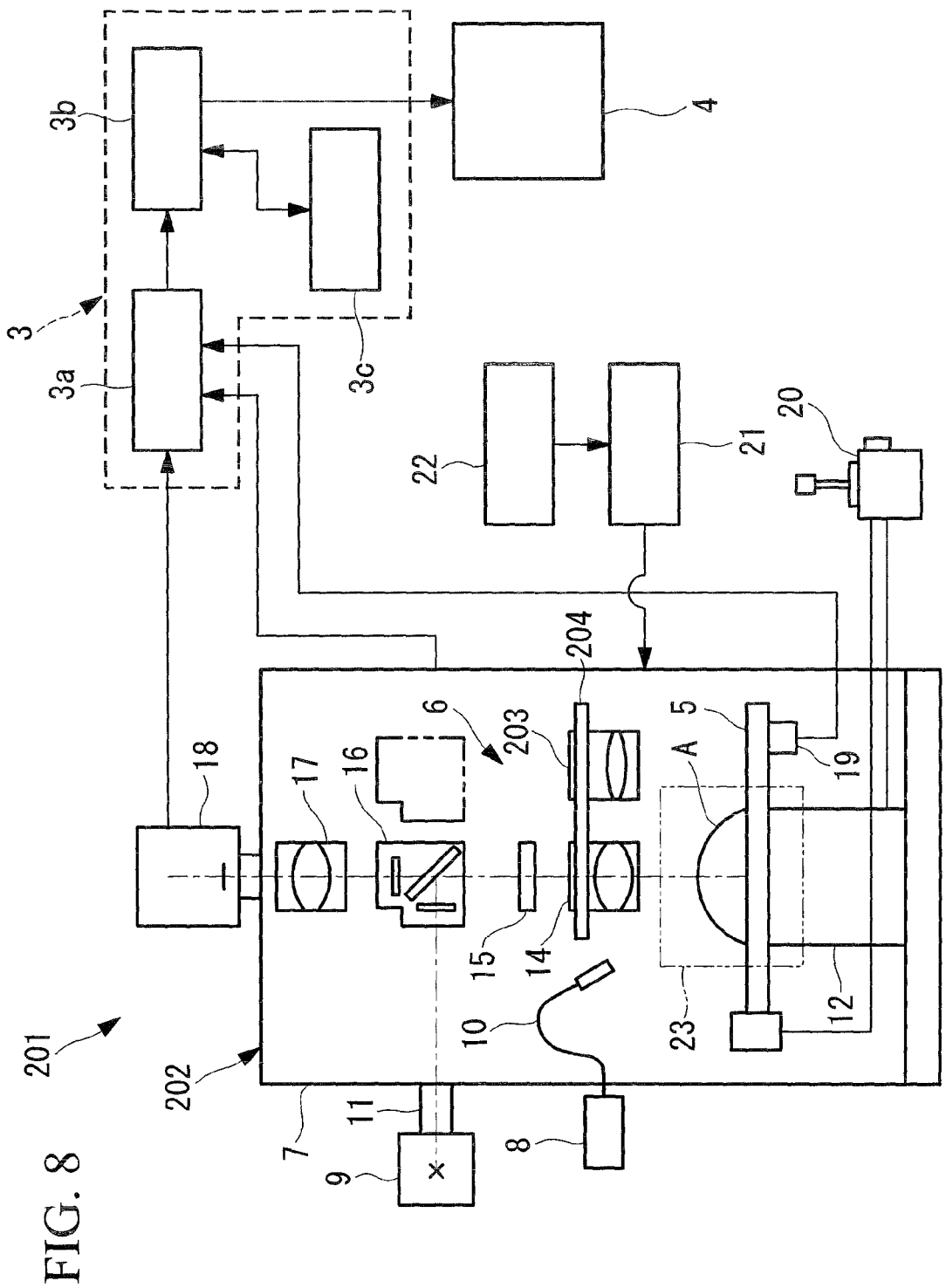
FIG. 8 is a diagram showing the overall configuration of a biological-specimen observation apparatus according to a second embodiment of the present invention.

As shown in FIG. 8, the biological-specimen observation apparatus 201 according to this embodiment is not provided with the zooming optical system 13 but is provided with a plurality of switchable objective lenses 14 and 203 having different focal distances. These objective lenses 14 and 203 are held by a revolver 204 so as to be selectively inserted in and removed from the observation optical system 6.

The objective lenses 14 and 203 have a viewing region as shown in FIGS. 9A, 9B and 9C. As shown in FIG. 9B, the objective lens 14 for observing the fluorescent material B in the specimen A has a viewing region smaller than that of the objective lens 203 and a high magnification. For example, its viewing region is 22.5 mm×30 mm and its magnification is about ×0.3.

On the other hand, as shown in FIG. 9A, the objective lens 203 is capable of observing the entire specimen A and has a viewing region larger than the objective lens 14 and a low magnification. For example, its viewing region is 120 mm×180 mm and its magnification is about ×0.05.

Figure 10A:
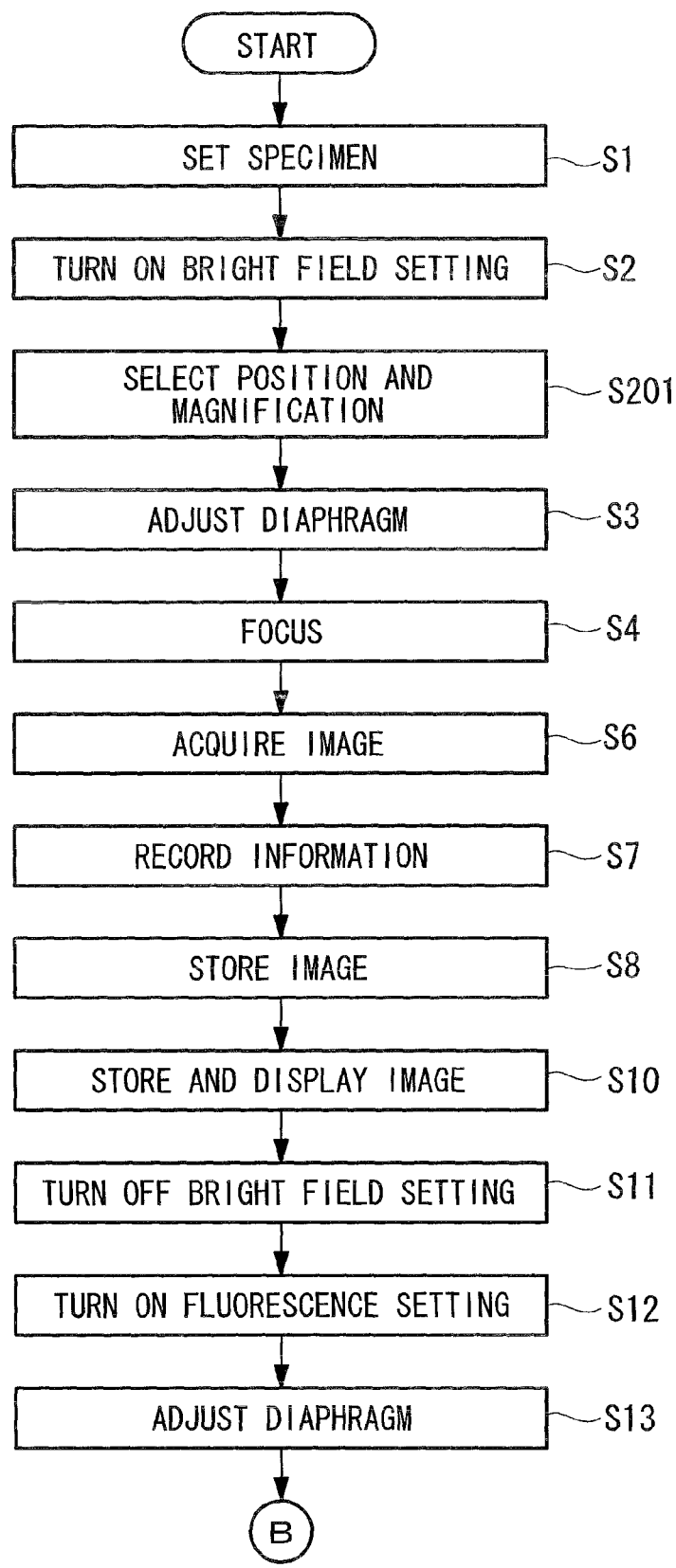
FIG. 10A is a flowchart describing the operation of the biological-specimen observation apparatus in FIG. 8.
Figure 10B:
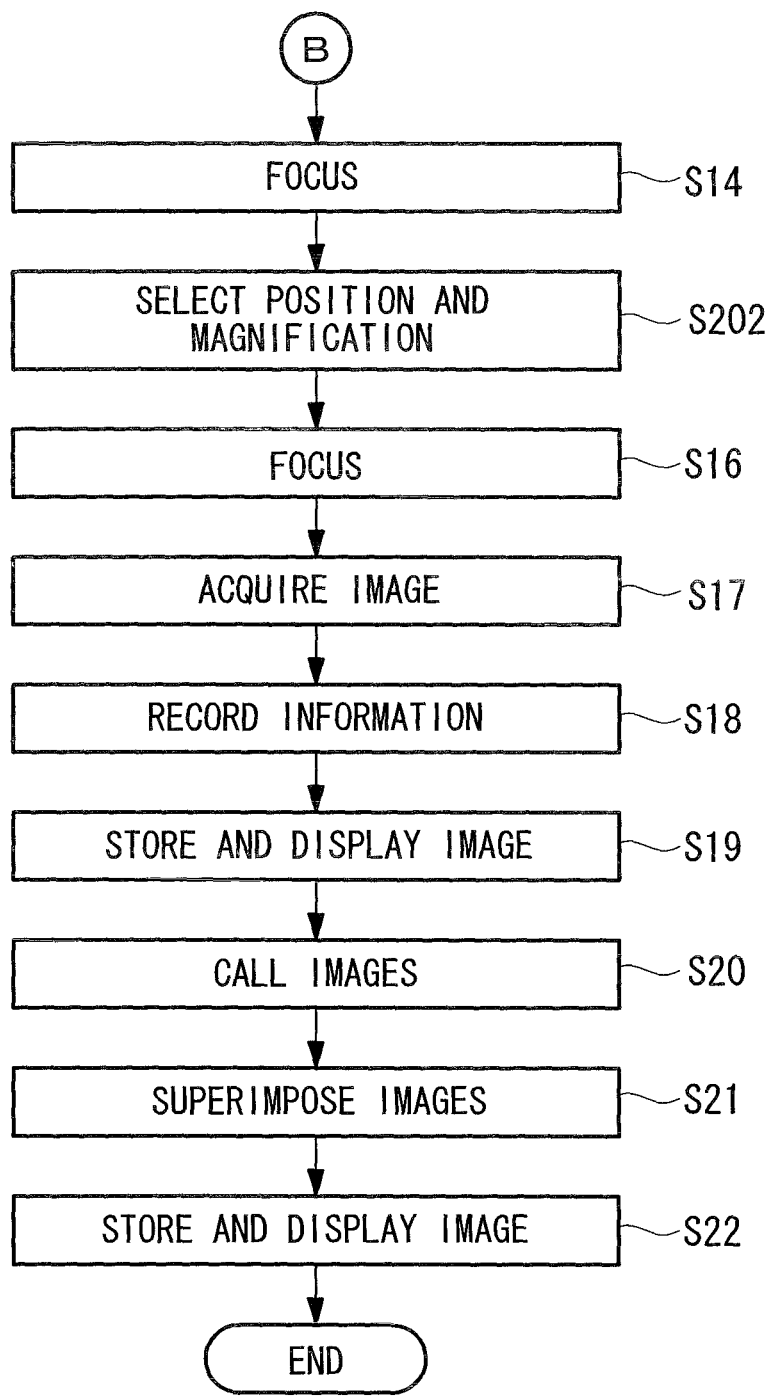
FIG. 10B is a flowchart describing the operation of the biological-specimen observation apparatus in FIG. 8.

FIGS. 10A and 10B shows a flowchart of observation using the biological-specimen observation apparatus 201 according to this embodiment.

In steps S1 to S10 for bright field observation, position adjustment and magnification selection are performed in new step S201 while a live image is being viewed. The position adjustment is performed using the operating unit 20, and the objective lens 203 having a wide viewing region and a low magnification is selected as an objective lens.

This does not include the step S5 in which the movement of the stage 5 and image acquisition are repeated and the image combining step S9 in the first embodiment.

Next, in steps S11 to S19 for fluorescence observation, switching between the objective lens 203 and 14 is performed in new step S202 by the operation of the revolver 204 instead of zooming during magnification selection. At that time, the objective lens 14 having a narrow viewing region and a high magnification is selected as an objective lens.

As shown in FIG. 9C, this embodiment has the same advantages as the first embodiment, namely, an image in which a clear fluorescence image is superimposed at the exact position of a bright field image can be obtained and the distribution of a fluorescent material in the specimen A can be quantitatively observed, and also the advantage of simplifying acquisition of a bright field image to allow the acquisition of the image in a shorter time.

Figure 11:
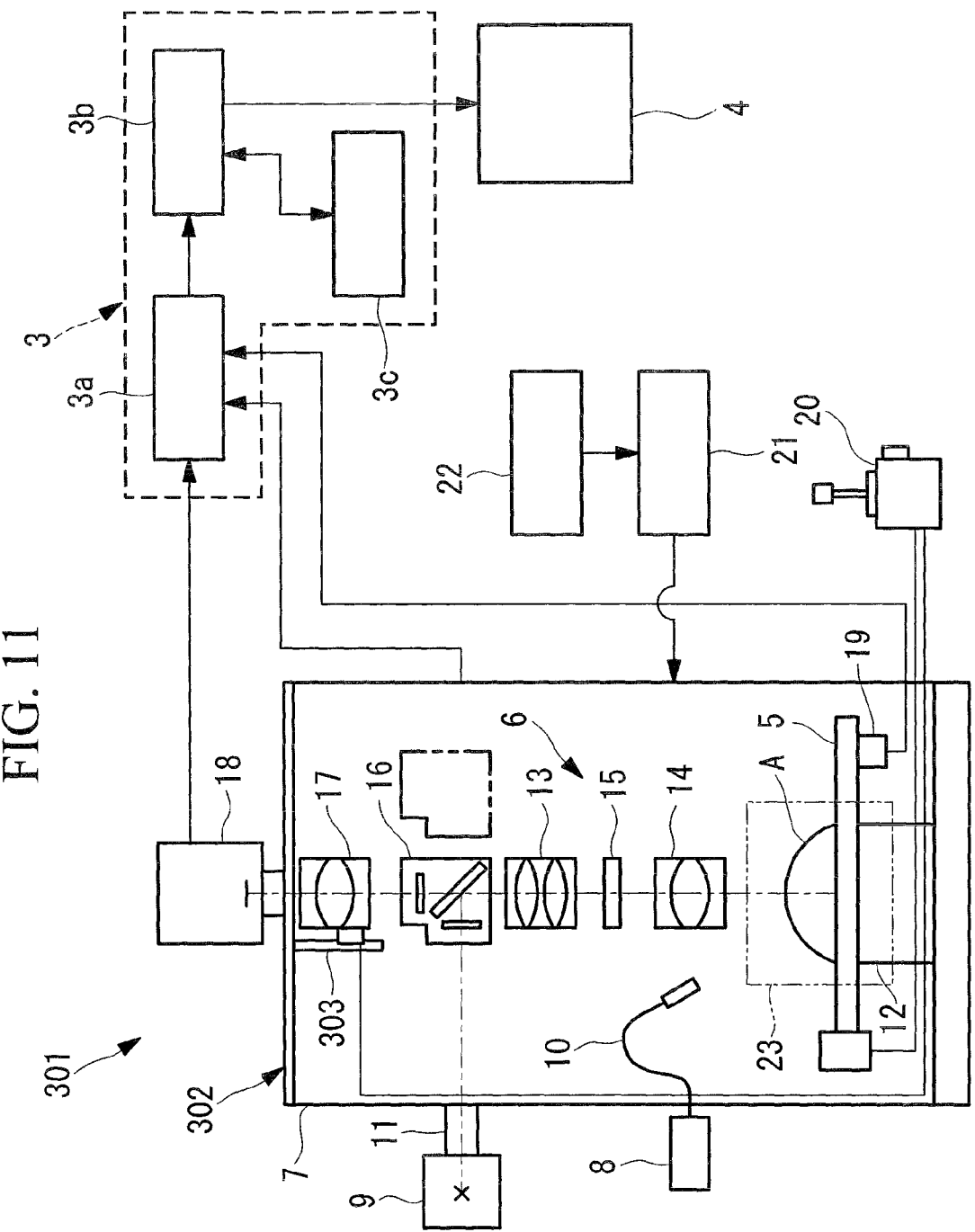
FIG. 11 is a diagram showing the overall configuration of a biological-specimen observation apparatus according to a third embodiment of the present invention.

Next, referring to FIG. 11, a biological-specimen observation apparatus 301 according to a third embodiment of the present invention will be described hereinbelow.

Also in the description of this embodiment, components having a configuration common to the above-described biological-specimen observation apparatus 1 according to the first embodiment are given the same reference numerals, and descriptions thereof will be omitted.

The biological-specimen observation apparatus 301 according to this embodiment is not provided with the focusing mechanism 12 for moving the stage 5 in the direction along the optical axis of the objective lens 14 but is provided with a linear motion mechanism 303 for moving the image-forming lens 17 in the direction along the optical axis. The linear motion mechanism 303 includes, for example, a linear motion guide having a motor serving as a driving source, a rail, and a slider, and a rack-and-pinion mechanism for transferring a driving force from the motor to the linear motion guide (not shown). The image-forming lens 17 is fixed to the slider, and the rail is fixed to an observation-apparatus main body 302. The linear motion guide is connected to the operating unit 20 so as to be operated also according to a signal from the operating unit 20.

This mechanism allows focusing by moving the image-forming lens 17 in the direction along the optical axis of the objective lens 14.

Thus, the biological-specimen observation apparatus 301 according to this embodiment has the same advantages as the biological-specimen observation apparatus 1 according to the first embodiment and also the advantage of reducing the problem of the changing image size during focusing to allow highly quantitative observation.

Figure 12:
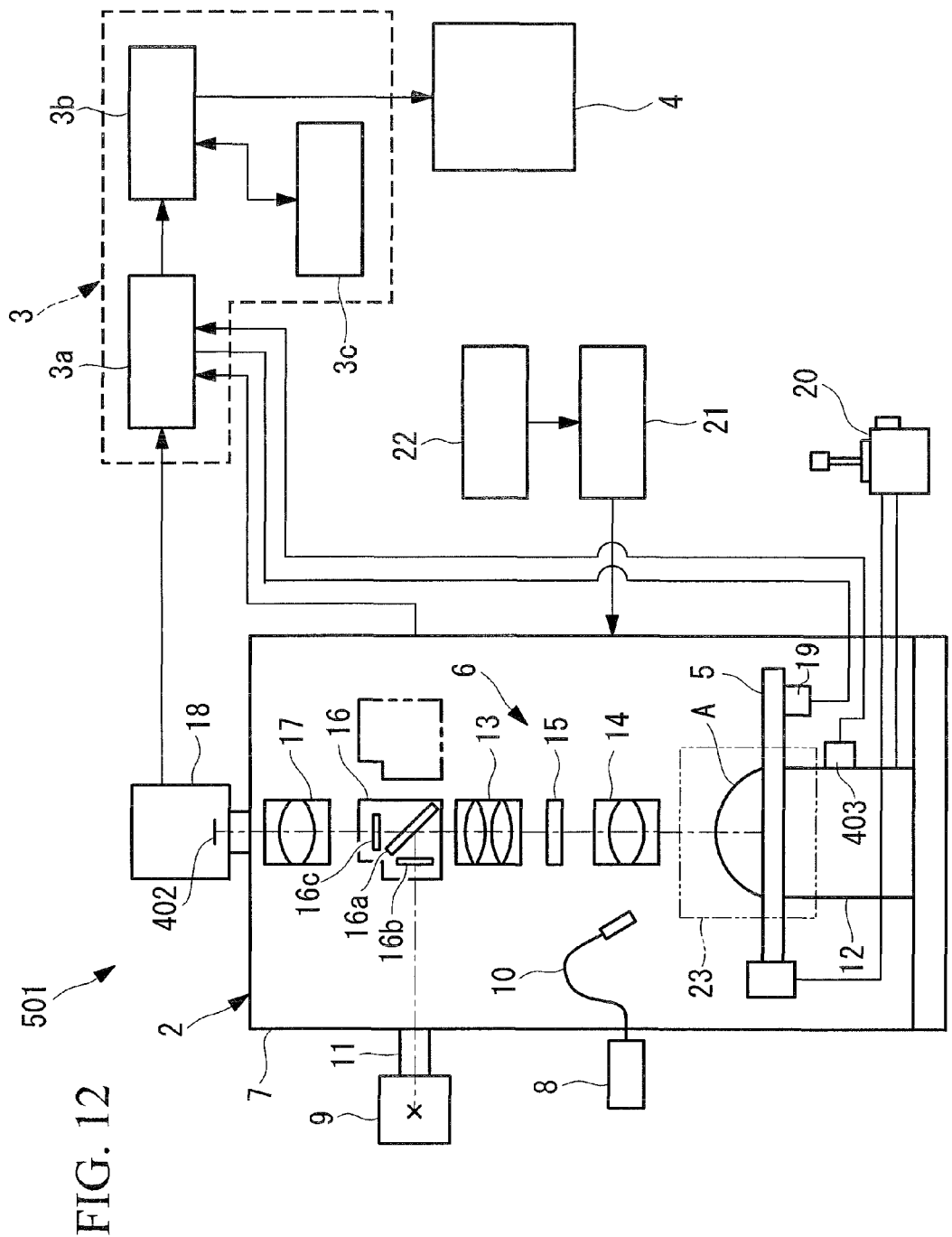
FIG. 12 is a diagram showing the overall configuration of a biological-specimen observation apparatus according to a fourth embodiment of the present invention.

Referring to FIG. 12, a biological-specimen observation apparatus 501 according to a fourth embodiment of the present invention will be described hereinbelow.

Also in the description of this embodiment, components having a configuration common to the above-described biological-specimen observation apparatus 1 according to the first embodiment are given the same reference numerals, and descriptions thereof will be omitted.

Figure 13:
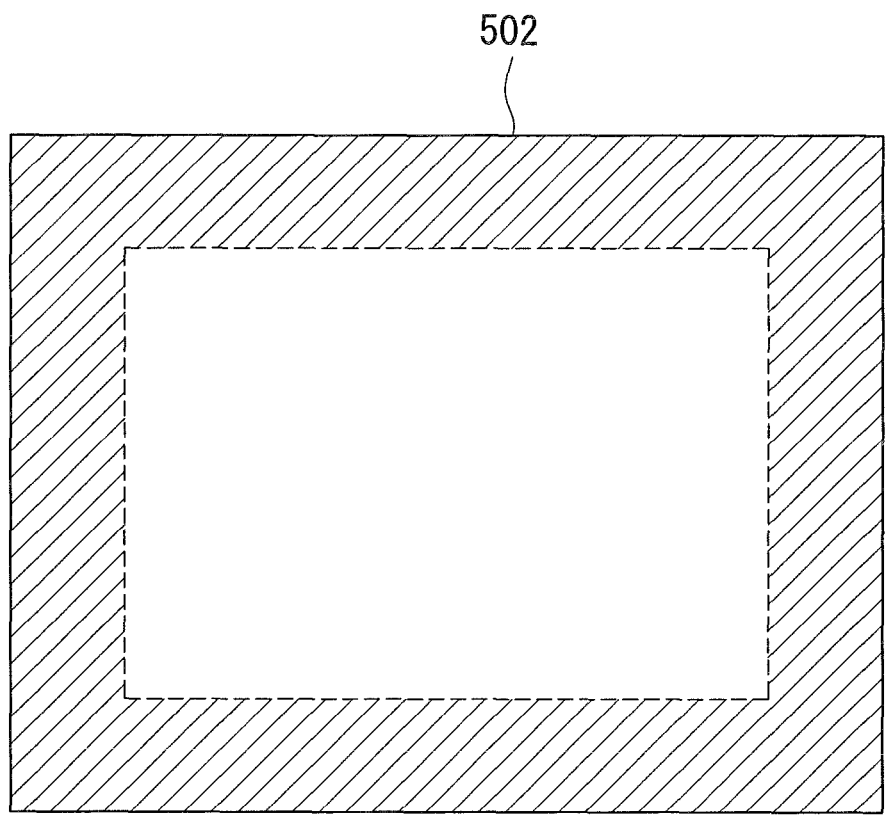
FIG. 13 is a diagram showing an image acquisition area of an image acquisition device.

In the biological-specimen observation apparatus 501 according to this embodiment, it is possible to partially disable the functioning of an image acquisition device 502 of the image acquisition unit 18. If the diagonally shaded area in FIG. 13 is disabled, an image of the dotted-line area in the image acquisition device 502 is obtained. Furthermore, information on the disabled part is sent to the information recording section 3a together with the image, so that dotted-line area information is added to the obtained information. Positional information of the focusing mechanism 12 is passed to the information recording section 3a by a position detector 503.

Figure 14A:
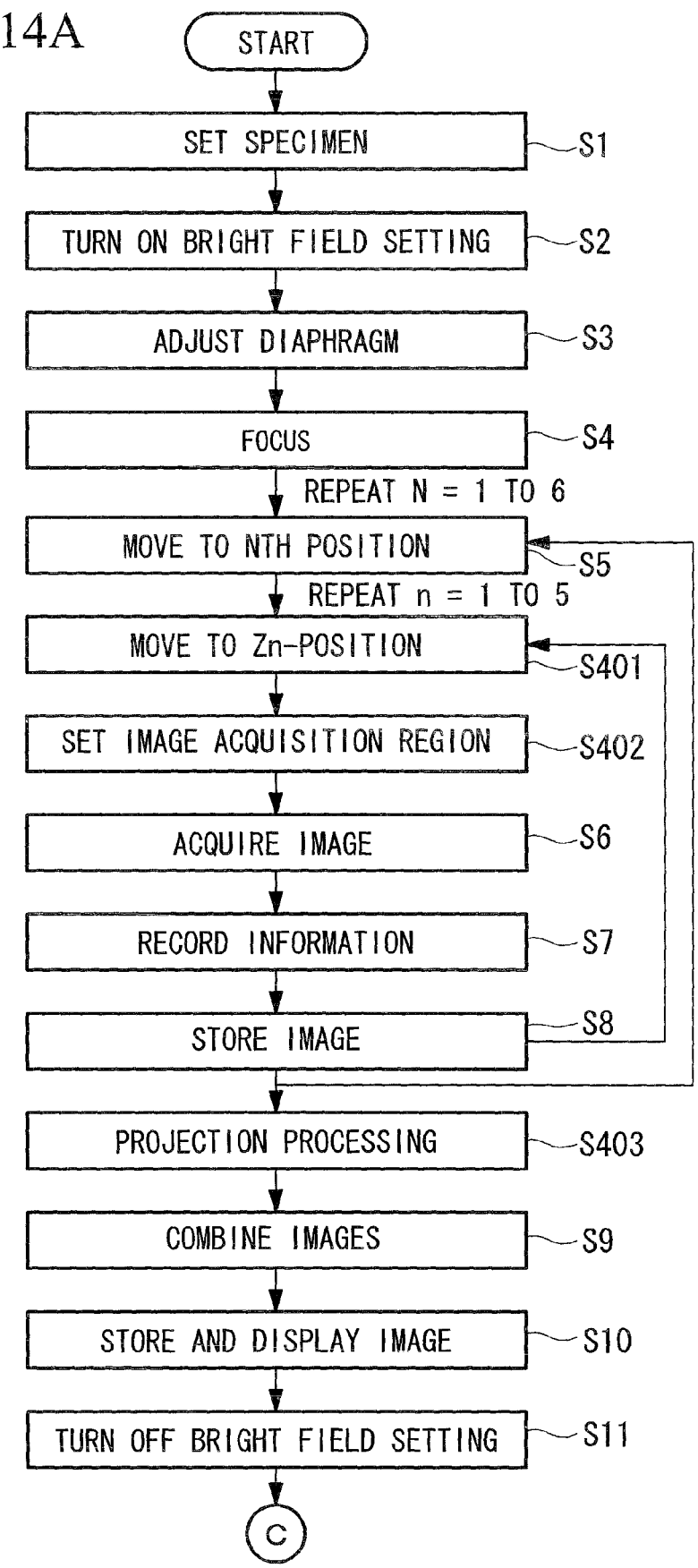
FIG. 14A is a flowchart describing the operation of the biological-specimen observation apparatus in FIG. 12.
Figure 14B:
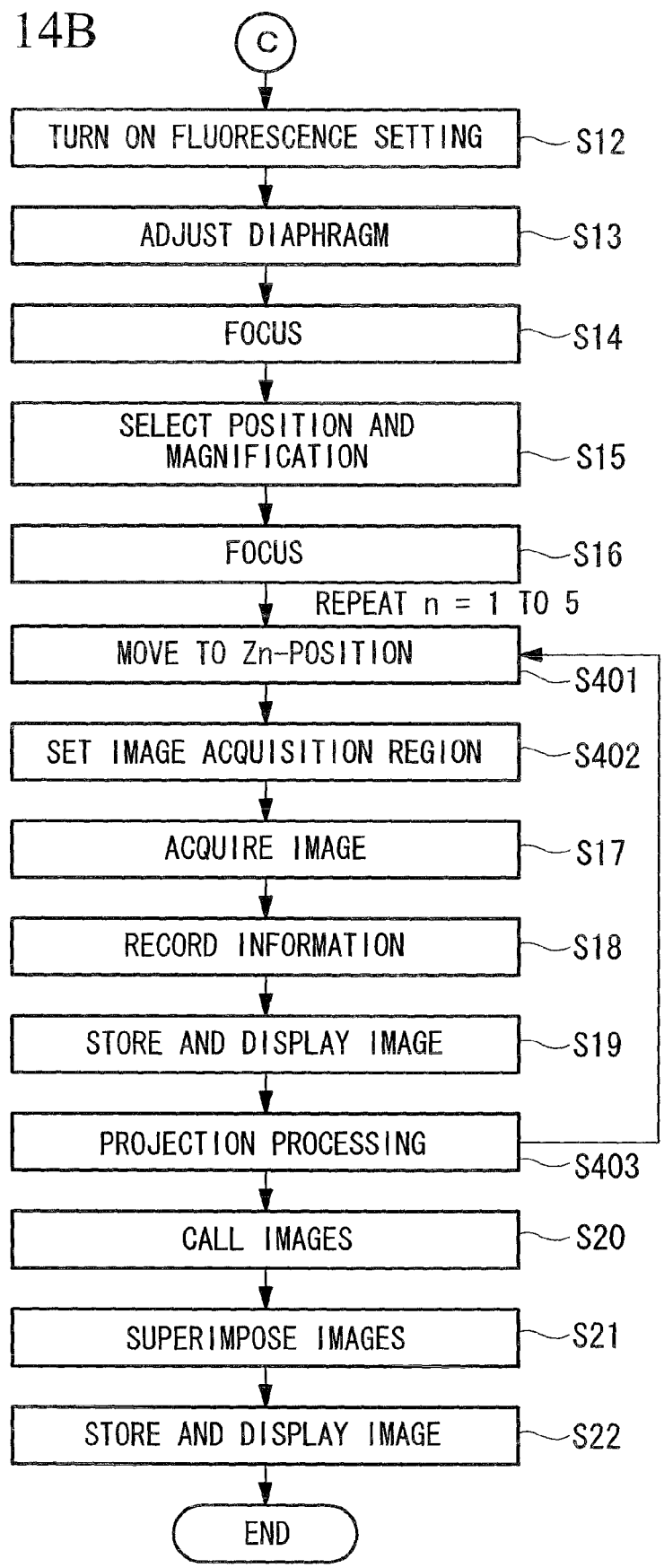
FIG. 14B is a flowchart describing the operation of the biological-specimen observation apparatus in FIG. 12.

FIGS. 14A and 14B shows a flowchart of observation according to this embodiment. Although the steps from the specimen setting step S1 to the focusing step S4 and the stage-5-position moving step S5 (N=1) are the same as those in the first embodiment, a Z-position moving flow (step S401) is added thereafter. This is for obtaining several images with different Z-positions, which are used as reference images for the following projection processing (step S403). For example, assuming that this flow is configured to obtain images by vertically moving the stage 5 in two steps from the focal point and that the amount of movement is 1 mm, Z1=P+2 mm, Z2=P+1 mm, Z3=P, Z4=P -1 mm, and Z5=P -2 mm are obtained, where P is a focal point obtained in step S4.

Subsequently, an image-acquisition-region setting step S402 for setting an area on the image acquisition device 502 to be disabled is provided between the Z-position moving step S401 and the image acquisition step S6. A limited acquired image is given information on the disabled area (acquired area) and Z-position information at the information recording section 3a and is stored in the image storage section 3b. A series of these observing operations is stored in the operation storage unit 22, so that the stage 5 and the image acquisition unit 18 are operated via the control unit 21 to allow image acquisition at the next position.

After image acquisition up to the sixth position is finished, the image processing section 3c executes the projection processing step S403. Here, in-focus portions are extracted from the images at individual Z-positions according to their brightness value information and are combined into one image. Thus, the images at the individual positions become a clear image without defocus even if the specimen A has surface irregularities.

After the projection processing step S403 is finished, the images are combined by matching the X and Y coordinate positions of the individual positions. This is set in the operation storage unit 22 so that the individual images are combined together without positional misalignment by using both the X and Y coordinates and the disabled area of the image acquisition device 502.

Although the following fluorescence observation step until focusing, position, and magnification setting is the same as in the first embodiment, Z-position moving (step S401) is added before the image acquisition step S17, and thereafter, the projection processing step S403 is performed. Although the amount of movement of Z-position does not necessarily need to be the same as that during bright field observation, they are basically based on the same operating principles. The projection processing step S403 is the same as that during the process of bright field observation.

The following steps of retrieving the bright field image in step S20, superimposing the bright field image and the fluorescence image together, and displaying the image are the same as in the first embodiment.

This can correct an out-of-focus {a defocused} area of an image due to surface irregularities of the specimen A and provide a clear image in which the entire image is in focus without blurring around the viewing field. Because the area to be acquired is limited, the image acquisition time can be reduced.

Although this embodiment excludes the periphery of the image by disabling the image acquisition device 502 of the CCD camera, the CCD camera may be configured to obtain an image as in the first embodiment and to trim the periphery of the image by postprocessing of the image. In this case, the moving coordinates of XY position need to be set in the operation storage unit 22 in consideration of the subsequent trimming process.

Figure 15A:
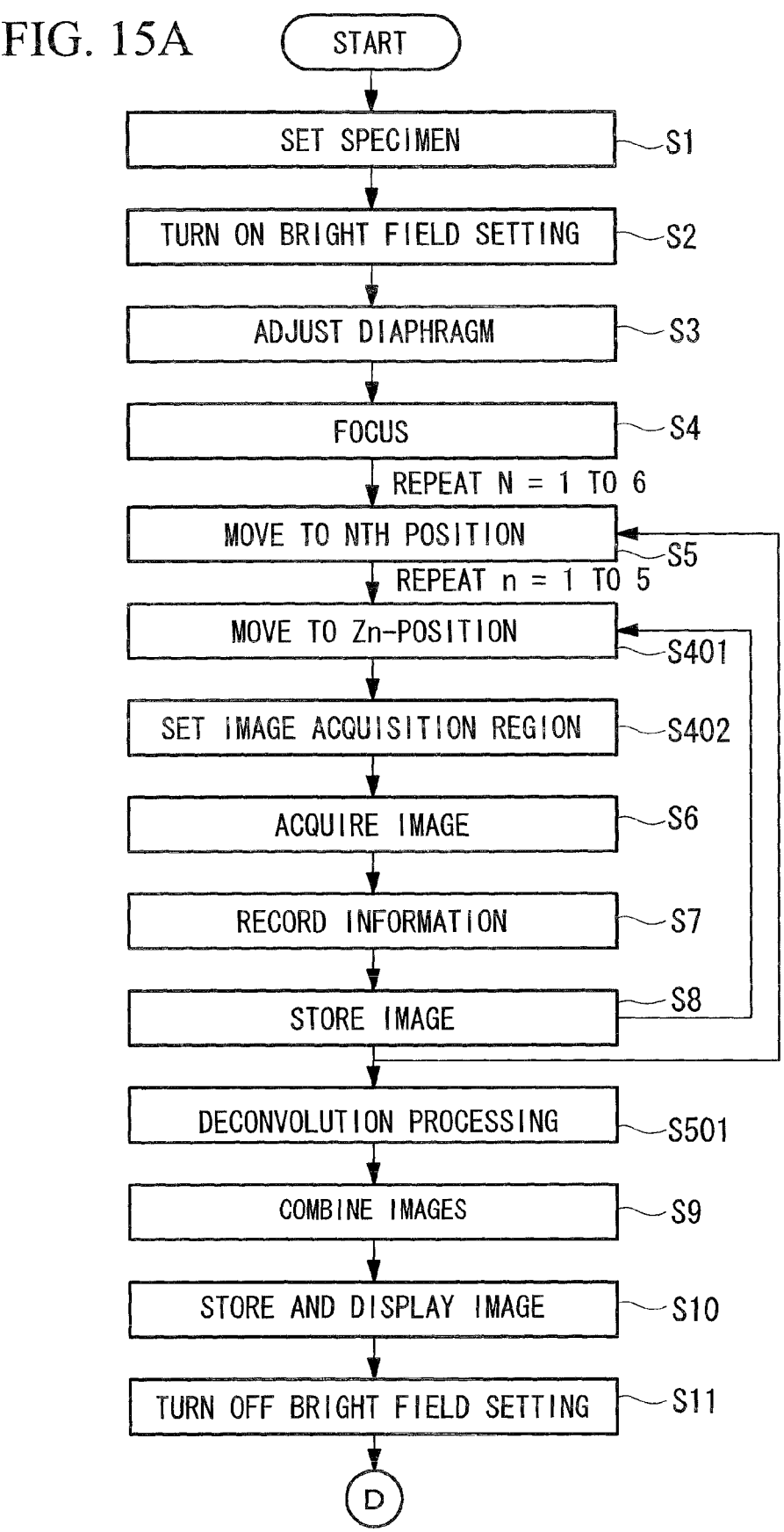
FIG. 15A is a flowchart describing a modification of the operation of the biological-specimen observation apparatus in FIG. 12.
Figure 15B:
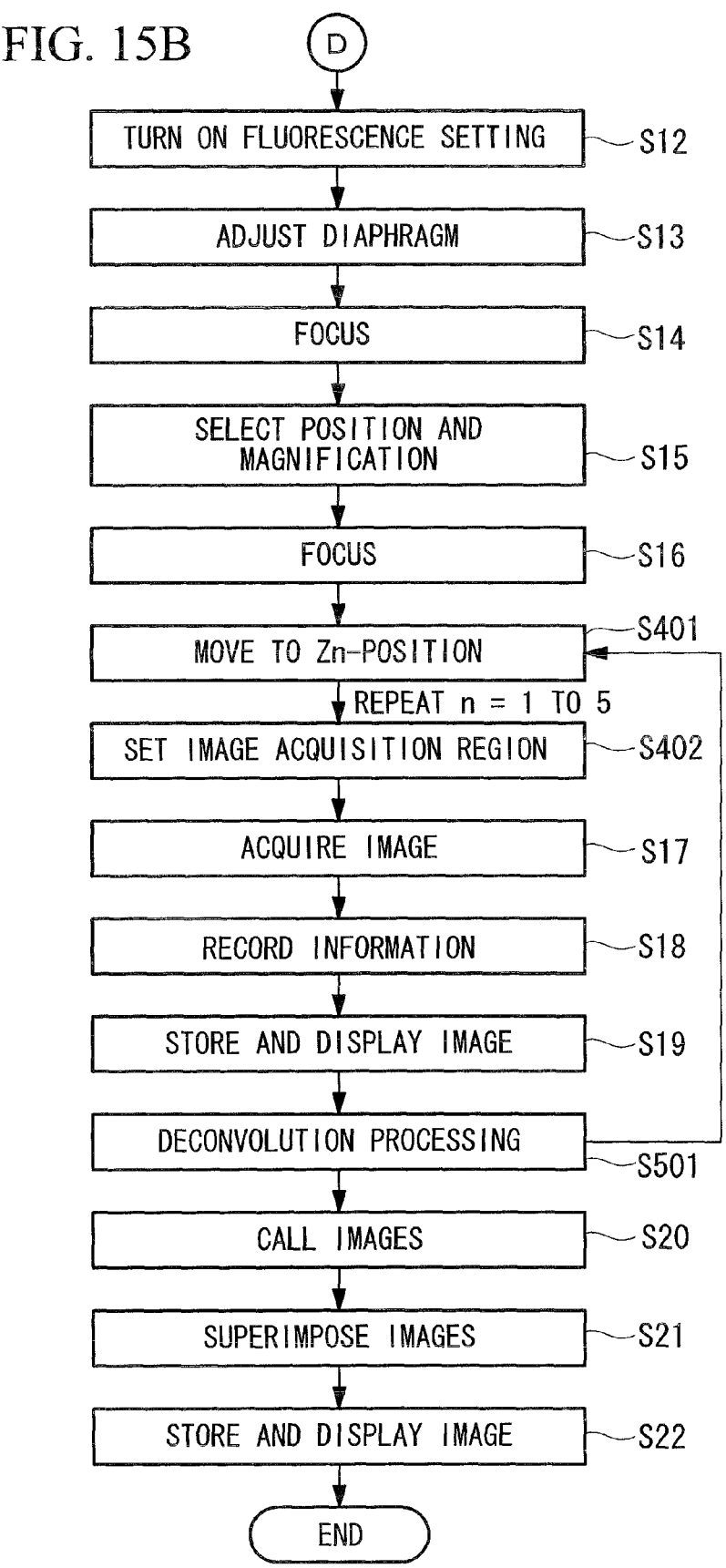
FIG. 15B is a flowchart describing a modification of the operation of the biological-specimen observation apparatus in FIG. 12.

Referring to a flowchart in FIGS. 15A and 15, a modification of the fourth embodiment will be described next. The apparatus configuration is the same as that in FIG. 12. In the flowchart of observation, instead of the projection processing step S403, a deconvolution processing step 501 is performed by the image processing section $3c_o$.

The deconvolution processing allows the images at the plurality of Z positions to be reconstructed as a 3D image. The unknown spaces among the Z-positions are estimated from the brightness distribution of the images to form a 3D image. Likewise, also in fluorescence observation, the obtained images are subjected to deconvolution, and finally XYZ positional information of a fluorescent material in the specimen A and volumetric information of fluorescent material can be obtained.

What is claimed is:

1. A biological-specimen observation apparatus comprising:
   a stage on which a specimen is to be mounted, the stage being movable to a plurality of positions, wherein the specimen is a small laboratory animal;
   an objective lens, disposed opposing the stage, that collects observation light from the specimen;
   a first light source that emits illumination light and irradiates the specimen at an angle with respect to the stage from a side toward the objective lens without passing through the objective lens;
   a second light source that emits excitation light and irradiates the specimen through the objective lens, along a direction coaxial with the optical axis of the objective lens;
   an image-forming lens that forms an image from the observation light from the specimen, collected by the objective lens, wherein the observation light comprises a light returning from the specimen as a result of the illumination light and a fluorescence emitted from the specimen as a result of the excitation light;
   an image acquisition unit that acquires the image of the specimen, formed by the image-forming lens;
   a position detection unit that obtains a positional information of the stage;
   an image control unit that moves the stage to a plurality of positions and causes the image acquisition unit acquire the image at each of the plurality of positions;
   an image storage unit that stores a plurality of the images obtained by the image acquisition unit and the positional information obtained by the position detection unit, the plurality of the images and the positional information being associated to each other;
   an image processing unit that generates one combined image by combining the plurality of the images stored by the image storage unit on the basis of the positional information stored in association with the plurality of the images; and
   a diaphragm device configured to change an aperture diameter between the objective lens and the image-forming lens.

2. The biological-specimen observation apparatus according to claim 1, further comprising:
   a focus detecting unit that detects focusing of the objective lens on the specimen; and
   an autofocusing unit that moves the stage in a direction along an optical axis of the objective lens on the basis of the detection result of the focus detecting unit so as to focus the objective lens on the specimen.

3. The biological-specimen observation apparatus according to claim 1, further comprising:
   a zooming mechanism, between the objective lens and the image-forming lens, that changes zoom magnification;
   wherein the image storage unit stores the zoom magnification in association with the plurality of the images and the positional information.

4. The biological-specimen observation apparatus according to claim 1, further comprising:
   an operation storage unit having an operation pattern for obtaining a plurality of images with different focal positions, wherein the
   image processing unit has a focus projection function.

5. The biological-specimen observation apparatus according to claim 1, wherein the image acquisition unit is a CCD camera, the observation apparatus having a function for changing an image acquisition region of the CCD camera and further comprising an information recording unit that records the obtained image acquisition region.

6. The biological-specimen observation apparatus according to claim 1, wherein the image processing unit has a function for trimming part of the stored images and combining processing them.

7. The biological-specimen observation apparatus according to claim 1, wherein the image processing unit has a deconvolution function.

8. The biological-specimen observation apparatus according to claim 1, wherein the image processing unit generates the one combined image at least by superimposing a bright field image obtained by emitting the illumination light from the first light source and a fluorescence image obtained by emitting the excitation light from the second light source.

9. The biological-specimen observation apparatus according to claim 8, wherein the fluorescence image combined by the image processing unit is subjected to image processing for changing the color in accordance with the brightness value.

10. The biological-specimen observation apparatus according to claim 8, wherein an area of the fluorescent image is a part of an area of the combined image.

11. The biological-specimen observation apparatus according to claim 10, wherein the image acquiring position selection unit moves the stage to a direction intersecting an observation optical axis.

12. The biological-specimen observation apparatus according to claim 1, wherein the position detector unit is a position detector provided on the stage.

13. The biological-specimen observation apparatus according to claim 1, further comprising a heat insulating unit for the specimen.

14. The biological-specimen observation apparatus according to claim 1, wherein the image acquisition unit acquires a bright field image obtained by emitting the illumination light from the first light source at each of the plurality of positions, the image processing unit generates one combined image by combining the plurality of images, the image acquisition unit acquires a fluorescence image obtained by emitting the excitation light from the second light source and being a part of a whole positional information of the combined image while the image processing unit superimposes the one combined image and the fluorescence image on the basis of the positional information stored in association with the plurality of the images.

15. A biological-specimen observation apparatus comprising:
- a stage for mounting a specimen, wherein the specimen is a small laboratory animal;
- an objective lens, disposed opposing the stage, that collects observation light from the specimen;
- a first light source that emits illumination light and irradiates the specimen at an angle with respect to the stage from a side toward the objective lens without passing through the objective lens;
- a second light source that emits excitation light and irradiates the specimen through the objective lens, along a direction coaxial with the optical axis of the objective lens;
- an image-forming lens that forms an image from the observation light from the specimen, collected by the objective lens, wherein the observation light comprises a light returning from the specimen as a result of the illumination light and a fluorescence emitted from the specimen as a result of the excitation light;
- an image acquisition unit that acquires a two dimensional image of the specimen, formed by the image-forming lens;
- an image acquiring position selection unit that selects a position of the specimen that the image acquisition unit acquires;
- an image control unit that directs the image acquisition unit to acquire the image at each of the plurality of positions selected by the image acquiring position selection unit;
- a positional information acquiring unit that obtains a positional information of the each of the plurality of positions of the acquired images;
- an image storage unit that stores a plurality of the images obtained by the image acquisition unit and the positional information of the images, the plurality of the images and the positional information being mutually associated;
- an image processing unit that generates one combined image by combining the plurality of the images stored by the image storage unit on the basis of the positional information stored in association with the plurality of the images; and
- a diaphragm device configured to change an aperture diameter between the objective lens and the image-forming lens.

16. A biological-specimen observation apparatus comprising:
- a stage on which a specimen is to be mounted, the stage being movable to a plurality of positions, wherein the specimen is a small laboratory animal;
- an objective lens, disposed opposing the stage, that collects observation light from the specimen;
- a first light source that emits illumination light and irradiates the specimen at an angle with respect to the stage from a side toward the objective lens without passing through the objective lens;
- a second light source that emits excitation light and irradiates the specimen through the objective lens, along a direction coaxial with the optical axis of the objective lens;
- an image-forming lens that forms an image from the observation light from the specimen, collected by the objective lens, wherein the observation light comprises a light returning from the specimen as a result of the illumination light and a fluorescence emitted from the specimen as a result of the excitation light;
- an image acquisition unit that acquires the image of the specimen, formed by the image-forming lens;
- a position detection unit that obtains a positional information of the stage;
- an image control unit that moves the stage to a plurality of positions and causes the image acquisition unit acquire the image at each of the plurality of positions;
- an image storage unit that stores a plurality of the images obtained by the image acquisition unit and the positional information obtained by the position detection unit, the plurality of the images and the positional information being associated to each other; and
- an image processing unit that generates one combined image by combining the plurality of the images stored by the image storage unit on the basis of the positional information stored in association with the plurality of the images.

* * * * *